(12) United States Patent
Epstein

(10) Patent No.: US 7,130,674 B1
(45) Date of Patent: Oct. 31, 2006

(54) UNITARY BIOMEDICAL ELECTRODE HAVING AN ATTACHMENT FLAP AND ITS ASSOCIATED METHOD OF MANUFACTURE

(76) Inventor: Stephen T. Epstein, 10 Lakeview Dr., Newtown, PA (US) 18940

( * ) Notice: Subject to any disclaimer, the term of this patent is extended or adjusted under 35 U.S.C. 154(b) by 124 days.

(21) Appl. No.: 10/778,816

(22) Filed: Feb. 17, 2004

(51) Int. Cl.
*A61B 5/04* (2006.01)

(52) U.S. Cl. ............................ 600/391; 607/152
(58) Field of Classification Search ............. 600/391, 600/392; 606/32; 607/152, 153
See application file for complete search history.

(56) References Cited

U.S. PATENT DOCUMENTS

| | | | | |
|---|---|---|---|---|
| 3,151,619 A | * | 10/1964 | Sullivan | 600/392 |
| 3,543,760 A | * | 12/1970 | Bolduc | 607/152 |
| 3,642,008 A | * | 2/1972 | Bolduc | 607/152 |
| 3,741,219 A | * | 6/1973 | Sessions | 607/153 |
| 4,370,984 A | * | 2/1983 | Cartmell | 600/385 |
| 5,511,548 A | | 4/1996 | Riazzi et al. | 128/641 |
| 5,824,033 A | * | 10/1998 | Ferrari | 607/142 |

\* cited by examiner

*Primary Examiner*—Lee S. Cohen
(74) *Attorney, Agent, or Firm*—Lamorte & Associates

(57) ABSTRACT

An electrode configuration and its method of manufacture. The electrode includes a pad of material having a first end, an opposite second end, a top surface and a conductive bottom surface. At least one fold line is provided in the pad of material between the first end and the second end. The pad of material is folded over along the fold lines to create a folded form. The folded form has a flap element that extends from one of the folds to the second end of the pad of material. The flap element enables a clip to attach to the pad of material without peeling the remainder of the pad of material from a person's skin.

14 Claims, 4 Drawing Sheets

UNITARY BIOMEDICAL ELECTRODE HAVING AN ATTACHMENT FLAP AND ITS ASSOCIATED METHOD OF MANUFACTURE

BACKGROUND OF THE INVENTION

1. Field of the Invention

In general, the present invention relates to electrodes that are placed on the skin of a patient. More particularly, the present invention relates to the physical structure of such electrodes and the methods used to manufacture such electrodes.

2. Description of the Prior Art

There are many types of medical equipment that gather and process electrical signals generated from within a patient's body. For instance, an electrocardiogram instrument detects electrical nerve impulses generated by the heart. Those detected impulses are then converted into a graphical representation so that the heart's nerve impulses can be viewed and analyzed by a doctor. Many other pieces of medical equipment exist that detect electrical impulses from other organs of the body, such as the brain, lungs and uterus.

In order for a piece of medical equipment to detect an electrical impulse from within the human body, some type of electrical lead must be attached between the medical equipment and the body. The electrical lead must mechanically attach to the body so that an electrical impulse generated within the body can be transmitted into the electrical lead and back to the medical equipment.

There are many types of electrical lead terminations that engage a patient's body and receive electrical impulses. Some of these prior art terminations are intrusive, in that they have an electrode lead that penetrates the skin or is introduced within an orifice of the body. However, for many types of medical testing, such as electrocardiograms, passive termination electrodes are used. A passive termination electrode is typically formed as a conductive pad. The conductive pad is glued, strapped or taped to the skin. The passive termination electrode detects electrical impulses through the skin without having to penetrate the skin. Such prior art passive termination electrodes are exemplified by U.S. Pat. No. 5,511,548 to Riazzi, entitled Biomedical Electrode Having A Secured One-Piece Conductive Terminal.

Passive termination electrodes that attach to the skin come in a wide assortment of sizes and configurations depending upon the intended application of the termination electrode. In many instances, the medical equipment that is connected to the termination electrodes, utilize wires with end clips. When such wires are used, the edge of the termination electrode is peeled up so that the end clip of the wire can clip onto the termination electrode. The weight of the end clip acts to peel the termination electrode away from the skin.

In many medical testing or monitoring procedures, multiple termination electrodes are attached to a patient's body. For instance, during an electrocardiogram, ten termination electrodes are commonly attached to a patient's chest and limbs. The positions of where the termination electrodes attach to the body are very specific. In order to obtain accurate data, each termination electrode must be attached to the body correctly and maintain proper contact to the skin throughout the duration of the test. However, during any test, it is unlikely that a patient will remain perfectly still. Rather, patents will move to some degree. As the patient moves, the raised edges of the termination electrodes tend to peel away from the skin. This is especially true if the termination electrode rubs against clothing or another part of the body as the patient moves.

Prior art termination electrodes are attached to the body and are then lifted along an edge to attach a wire with an end clip. During the course of testing, the raised edges of the termination electrodes tend to twist and peel away from the skin. This creates poor contact between the electrode and the skin, which leads to test failures.

A need therefore exists for an improved passive termination electrode that enables a wire with a clip termination to attach to the termination electrode without the need of partially peeling up any edge of the termination electrode. This need is met by the present invention device as it is described and claimed below.

SUMMARY OF THE INVENTION

The present invention is a new electrode configuration and its method of manufacture. The electrode is applied to a person's skin, where it provides electrical contact with a person's skin for a medical testing or monitoring device. The electrode includes a pad of material having a first end, an opposite second end, a top surface and a conductive bottom surface. At least one fold line is provided in the pad of material between the first end and the second end. The pad of material is folded over along the fold lines to create a folded form. The folded form has a flap element that extends from one of the folds to the second end of the pad of material. The flap element enables a clip to attach to the pad of material without peeling the remainder of the pad of material from a person's skin.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Figure 1:
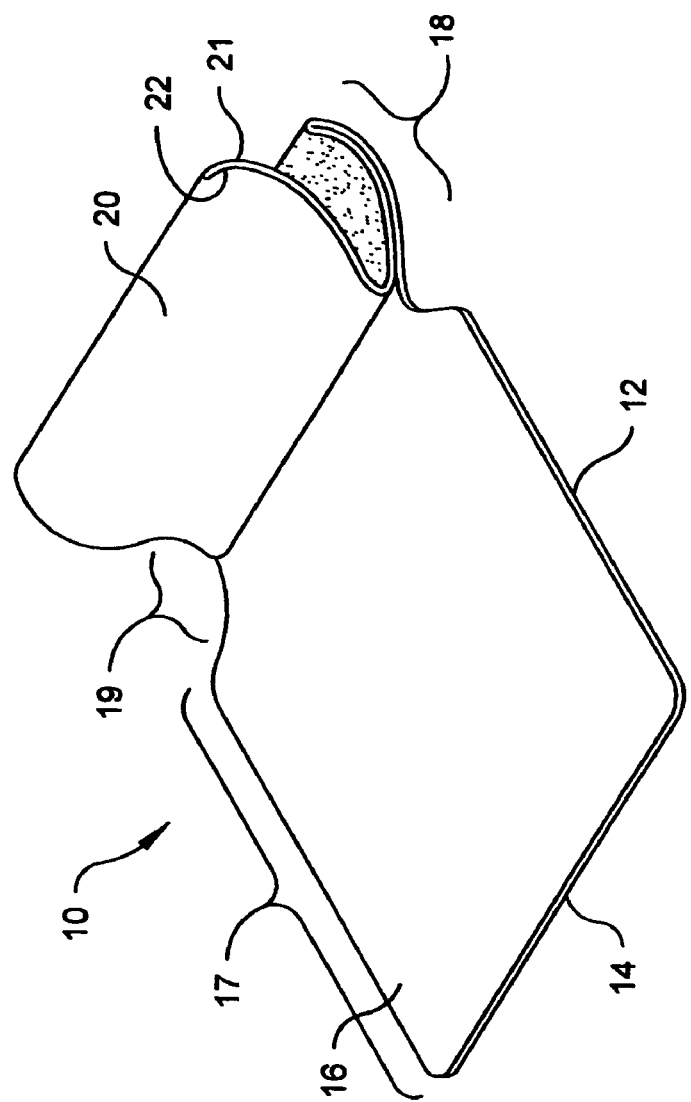
FIG. 1 is a perspective view of a first exemplary embodiment of a termination electrode in accordance with the present invention.

Referring to FIG. 1, a first exemplary embodiment of the present invention termination electrode 10 is shown. The termination electrode 10 has a base pad 12 that attaches to the skin of a patient. The base pad 12 is a composite structure. The base pad 12 has a conductive bottom surface 14 and a non-conductive top surface 16. As will later be explained in more detail, the bottom surface 14 is coated with a conductive adhesive that enables the bottom surface 14 of the base pad 12 to adhesively bond to a patient's skin.

The termination electrode 10 can have many different shapes, such as rectangular, square or round. However, in the example embodiment that is shown, the termination electrode 10 has a complex shape that includes a square primary section 17 and an oval secondary section 18 that are interconnected along a reduced neck region 19.

A flap element 20 extends above the oval secondary section 18 of the base pad 12. The flap element 20 in the shown embodiment is the same shape as the oval secondary section 18 of the base pad 12. However, this need not be the case. The flap element 20 can be larger or smaller than the oval secondary section of the base pad 18 underlying it, depending upon the aesthetic requirements of the manufacturer.

The flap element 20 has a bottom surface 21 and a top surface 22. The bottom surface 21 of the flap element 20 is conductive and is electrically interconnected with the bottom surface 14 of the base pad 12, as will later be explained.

Figure 2:
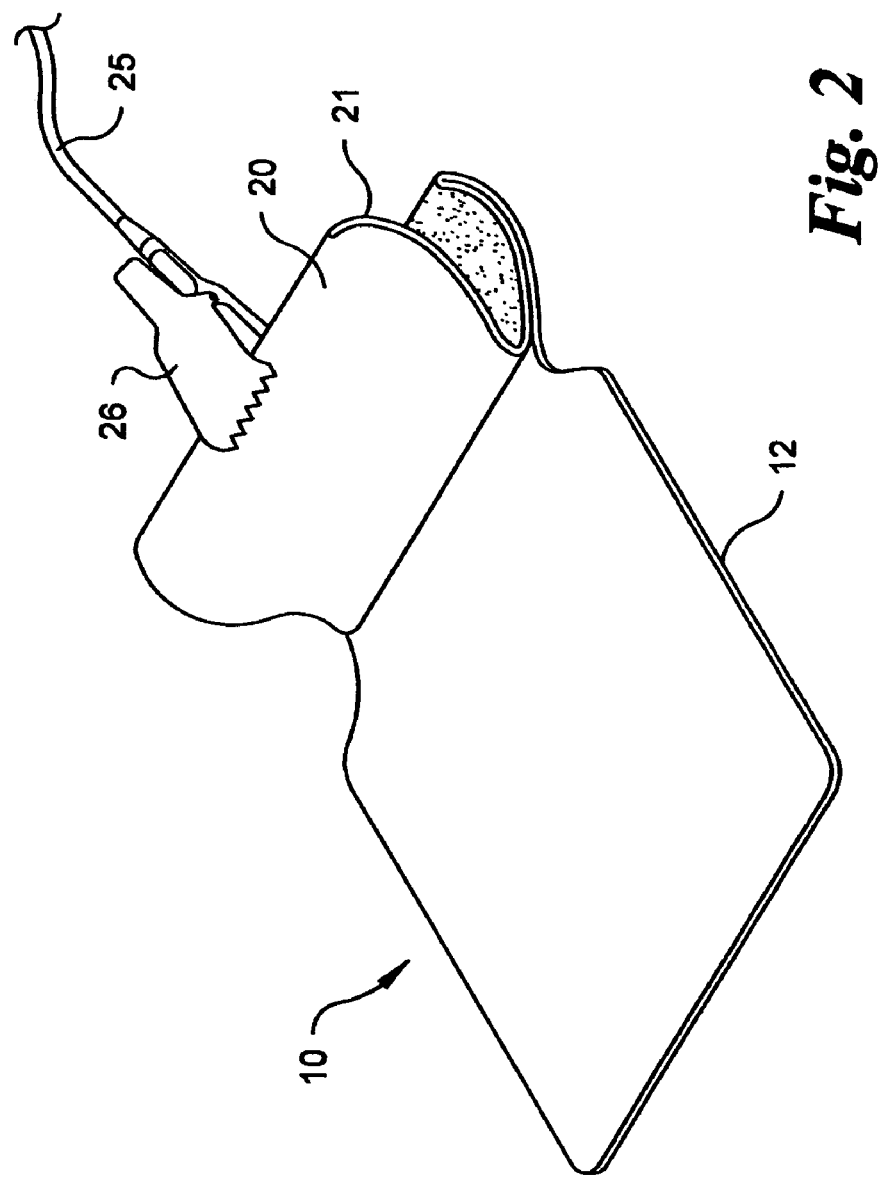
FIG. 2 is a perspective view of the embodiment of FIG. 1 shown in conjunction with a wire lead having a clip end.

Referring to FIG. 2, a wire 25 is shown having an end clip 26. The end clip 26 attaches to the flap element 20. One of the jaws of the end clip 26 contacts the bottom surface 21 of the flap element 20, thus creating an electrical interconnection between the wire 25 and the termination electrode 10. However, although the end clip 26 attaches to the flap element 20, the base pad 12 can remain flush against the surface of a patient's skin. Thus, the attachment of the end clip 26 to the electrode termination 10 has no adverse effect upon the adhesive attachment of the base pad 12 to a patient's skin.

Figure 3:
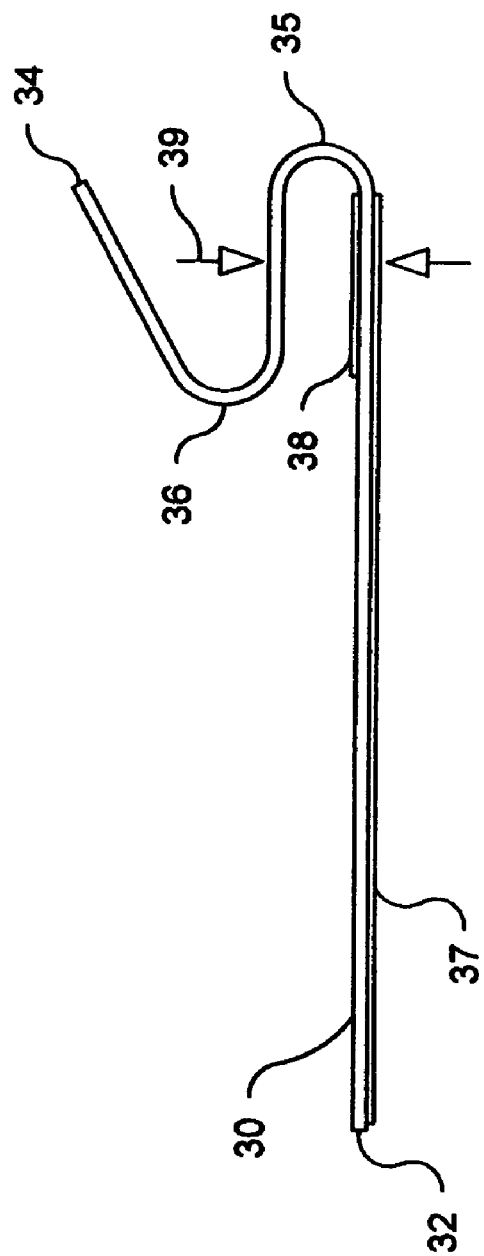
FIG. 3 is a side view of the embodiment of FIG. 1 shown in a partially unfolded configuration.

Referring to FIG. 3, it can be seen that the termination electrode 10 is unitarily constructed from a single composite sheet 30 that is selectively folded and cut. Each termination electrode has a first end 32 and a second end 34. Two fold lines 35, 36 are disposed between the first end 32 and the second end 34 to complete the shape of the termination electrode 10. A layer of conductive adhesive 37 is deposited on the bottom surface of the composite sheet 30 in between the first end 32 and the first fold line 35. A second layer of adhesive 38 is applied to the top surface of the composite sheet 30 proximate the first fold line 35.

The composite sheet 30 is folded over the second layer of adhesive 38 and is pressed onto the second layer of adhesive 38 as is indicated by arrows 39. The composite sheet 30 is then again folded over at the second fold line 36, wherein the flap element 20 is formed between the second fold line 36 and the second end 34.

Figure 4:
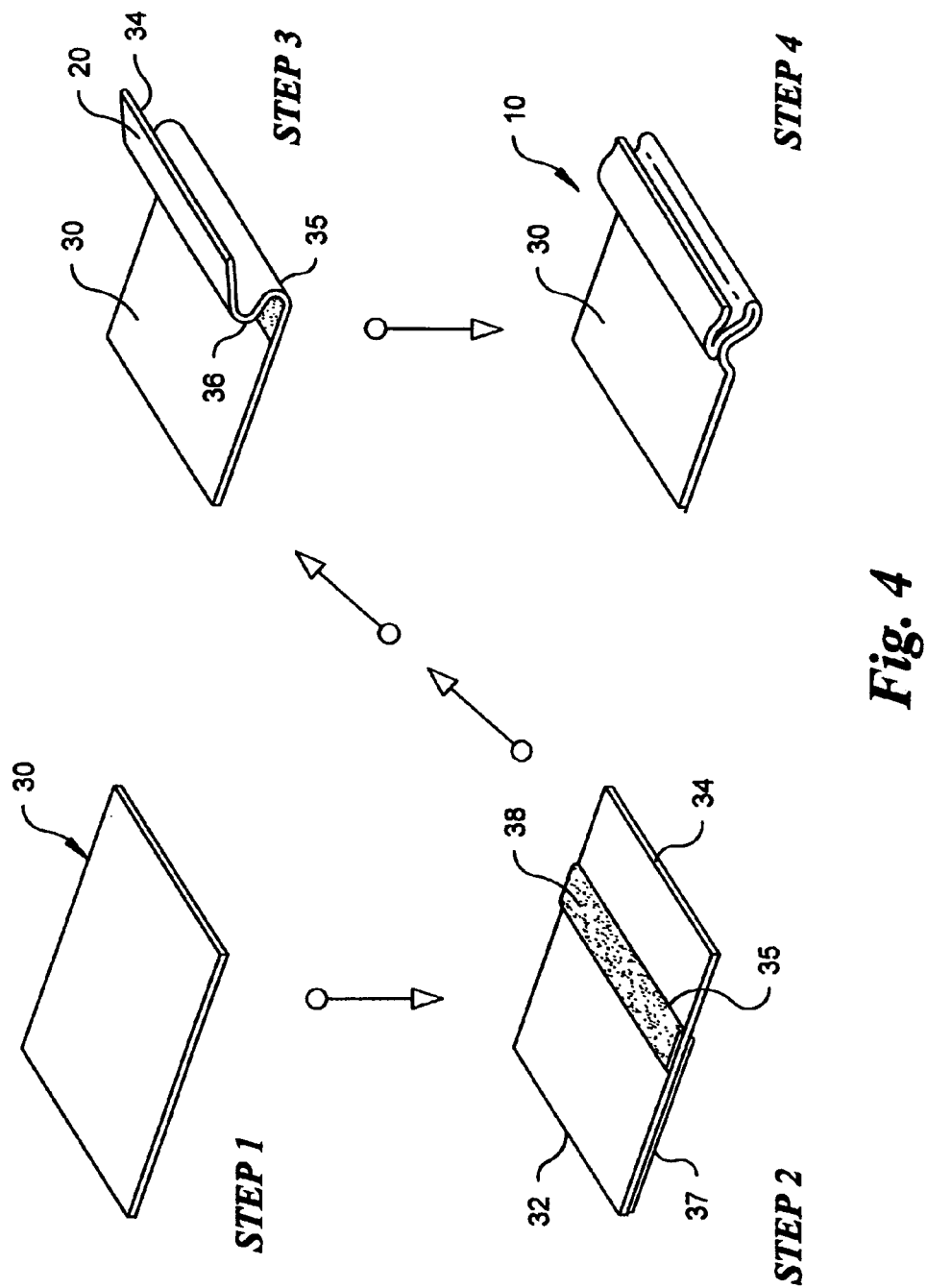
FIG. 4 is a four-step schematic illustration of an exemplary embodiment of manufacturing a termination electrode in accordance with the present invention.

With the structure of the electrode termination being fully described, the method of manufacturing the electrode termination can now be better understood. Referring to FIG. 4, it can be seen that in step one of the exemplary manufacturing method, a composite sheet 30 is provided. The composite sheet 30 has a traditional electrode construction, wherein a conductive bottom surface and a paperbacked top surface are provided. Many composite constructions are also used in the prior art in the formation of termination electrodes. Most any flexible prior art composite construction can be adapted for use as the composite sheet 30 of the present invention.

In accordance with step 2 of the exemplary manufacturing method, a layer of conductive adhesive 37 is applied to the bottom surface of the composite sheet 30 from the first end 32 to the first fold line 35. A second layer of adhesive 38 is also applied along the top surface of the composite sheet 30 in an area immediately adjacent the first fold line 35.

In accordance with step 3 of the exemplary manufacturing method, the portion of the composite sheet 30 between the first fold line 35 and the second end 34 is folded up and over itself in a generally S-shaped folding pattern. When folded in such a pattern, a section of the top surface of the composite sheet 30 folds over the second layer of adhesive 38 that has been applied to the top surface. The section of the composite sheet 30 between the second fold line 36 and the second end 34, hangs free as the flap element 20. Since the composite sheet 30 is continuous from the first end 32 to the second end 34, the conductive bottom surface of the flap element remains electrically interconnected with the bottom surface of the remainder of the composite sheet 30.

Referring to step 4 of the exemplary method of manufacture, it can be seen that the folded and glued composite sheet 30 is then cut to the desired size and shape to complete the formation of the electrode termination 10.

In the method set forth in FIG. 4, the formation of only a single electrode termination is shown. It will be understood that commercial manufacturing methods will use large sheets of material where multiple electrode terminations will be manufactured simultaneously. In the last step of cutting, individual electrode terminations are cut away from large sheets.

It will be understood that the embodiment of the present invention termination electrodes that is described and illustrated herein is merely exemplary and a person skilled in the art can make many variations to the embodiments shown without departing from the scope of the present invention. All such variations, modifications and alternate embodiments are intended to be included within the scope of the present invention as defined by the appended claims.

What is claimed is:

1. An electrode device for providing electrical contact with a person's skin, said device comprising:
   a pad of material having a first end, an opposite second end, a top surface and a conductive bottom surface;
   a first fold line disposed between said first end and said second end;
   a second fold line disposed between said first fold line and said second end;
   wherein said pad of material is folded over along said first fold line so that adjacent sections of said top surface of said pad of material abut proximate said first fold line; and
   wherein said pad of material is folded along said second fold line, creating a flap between said second fold line and said second end.

2. The device according to claim 1, wherein said first fold line, said second fold line and said first end are parallel.

3. The device according to claim 1, wherein said adjacent sections of said top surface are adhesively joined together proximate said first fold line.

4. The device according to claim 1, further including a layer of adhesive on said bottom surface of said pad of material between said first end and said first fold line.

5. An electrode device for providing electrical contact with a person's skin, comprising:
   a pad base having a top surface and a conductive bottom surface;
   a flap element extending from said top surface of said pad base, said flap element having a conductive surface that is electrically interconnected with said conductive bottom surface of said pad base;
   wherein said pad base and said flap element are part of a unitary sheet of material, and said flap element is formed by creating a generally S-shaped fold in said unitary sheet of material.

6. The device according to claim 5, wherein said pad base and said flap element are part of a common sheet of material that has a first end, an opposite second end, a top surface and a conductive bottom surface;
   a first fold line disposed between said first end and said second end;
   a second fold line disposed between first fold line and said second end;

wherein said sheet of material is folded over along said first fold line so that adjacent sections of said top surface of said sheet of material abut proximate said first fold line; and wherein said sheet of material is folded along said second fold line, creating a said flap element between said second fold line and said second end.

7. The device according to claim 6, wherein said first fold line, said second fold line and said first end are parallel.

8. The device according to claim 7, further including a layer of adhesive on said bottom surface of said pad base between said first end and said first fold line.

9. The device according to claim 6, wherein said adjacent sections of said top surface are adhesively joined together proximate said first fold line.

10. A method of forming an electrode for providing electrical contact to a person's skin, said method comprising the steps of:

providing a planar sheet of material having a first end, a second end, a top surface and a conductive bottom surface;

forming multiple folds in said planar sheet between said first end and said second end to create a folded form, said multiple folds including first fold and a last fold, wherein said planar sheet of material lay in a first plane between said first end and said first fold, and wherein said folded form includes a flap element that extends in a second plane between said last fold and said second end.

11. The method according to claim 10, wherein said step of forming multiple folds includes forming a generally S-shaped fold in said sheet of material.

12. The method according to claim 10, further including the step of applying adhesive to said bottom surface of said sheet of material between said first end and said first fold.

13. The method according to claim 10 further including the step of applying adhesive to said top surface of said sheet of material between said first fold and said last fold.

14. The method according to claim 10, further including the step of cutting said folded form into a predetermined shape.

* * * * *